(12) United States Patent
Apostolico et al.

(10) Patent No.: US 8,290,716 B2
(45) Date of Patent: Oct. 16, 2012

(54) METHODS AND SYSTEMS FOR CONSERVATIVE EXTRACTION OF OVER-REPRESENTED EXTENSIBLE MOTIFS

(75) Inventors: Alberto Apostolico, Atlanta, GA (US); Matteo Comin, Venice (IT); Laxmi Priya Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/882,633

(22) Filed: Sep. 15, 2010

(65) Prior Publication Data
US 2011/0004416 A1  Jan. 6, 2011

Related U.S. Application Data

(62) Division of application No. 11/471,552, filed on Jun. 21, 2006, now Pat. No. 7,865,313.

(51) Int. Cl.
*G06F 19/00* (2011.01)
*G06F 15/00* (2006.01)
(52) U.S. Cl. .............................. 702/20; 700/1
(58) Field of Classification Search .......................... None
See application file for complete search history.

(56) References Cited

U.S. PATENT DOCUMENTS
6,571,230 B1   5/2003   Parida

OTHER PUBLICATIONS

Sinha et al. Discovery of novel transcription factor binding sites by statistical overrrepresentation Nucleic Acids Research vol. 30, pp. 5549-5560 (2002).*
Apostolico et al. "Conservative extraction of over-represented extensible motifs". Bioinformatics vol. 21 Suppl. 1 pp. i9-i18 (2005).
Brazma et al. "Approaches to the Automatic Discovery of Patterns in Biosequences". Journal of Computational Biology vol. 5, pp. 279-305 (1998).
Anne Bergeron et al. "The Algorithmic of Gene Teams", WABI 2002, LNCS 2452, pp. 464-476, 2002.
Anne Bergeron et al. "On the Similarity of Sets of Permutations and Its Applications to Genome Comparison", COCOON 2003, LNCS 2697, pp. 68-79, 2003.
Xin He et al. "Identifying Conserved Gene Clusters in the Presence of Orthologous Groups", RECOMB'04, Mar. 27-31, 2004, pp. 272-280.

* cited by examiner

*Primary Examiner* — John S Brusca
(74) *Attorney, Agent, or Firm* — McGinn IP Law Group, PLLC (57) ABSTRACT

Methods and systems of extracting extensible motifs from a sequence include assigning a significance to extensible motifs within the sequence based upon a syntactic and statistical analysis, and identifying extensible motifs having a significance that exceeds a predetermined threshold.

14 Claims, 3 Drawing Sheets

METHODS AND SYSTEMS FOR CONSERVATIVE EXTRACTION OF OVER-REPRESENTED EXTENSIBLE MOTIFS

The present application is a Divisional Application of U.S. patent application Ser. No. 11/471,552, filed on Jun. 21, 2006 now U.S. Pat. No. 7,865,313, the entire content of which is incorporated herein by reference.

BACKGROUND OF THE INVENTION

1. Field of the Invention

The present invention generally relates to a method and a system for extraction of extensible motifs. More particularly, the present invention relates to a method and system for extraction of extensible motifs using combinatorial and statistical pruning.

2. Description of the Related Art

The discovery of a motif in a biosequence is frequently torn between the rigidity of the model on the one hand and the abundance of candidates on the other. In particular, the variety of motifs described by strings that include "don't care" patterns escalates exponentially with the length of the motif, and this only gets worse if a "don't care" is allowed to stretch up to some prescribed maximum length. This circumstance tends to generate daunting computational burdens, and often gives rise to tables that are impossible to visualize and digest. This is unfortunate, as it seems to preclude precisely those massive analyses that have become conceivable with the increasing availability of massive amount of genomic and protein data. While part of the problem is endemic, another part of it seems rooted in the various characterizations offered for the notion of a motif, that are typically based either on syntax or on statistics alone.

The discovery of motifs in bio-sequences is attracting increasing interest due to the perceived multiple implication of motifs in biological structure and function. The approaches to motif discovery may be partitioned into two main classes. In the first class, the sample string is tested for occurrences of motifs in a family of a priori defined, abstract models or templates. The second class of approaches assumes that the search may be limited to substrings in the sample or to some more or less controlled neighborhood of those substrings. The approaches in the first class are more rigorously justifiable, but often pose daunting computational burdens. Those in the second class tend to be computationally viable but rest on more shaky methodological grounds.

The characterizations offered for the notion of a motif could be partitioned roughly into statistical and syntactic. In a typical statistical characterization, a motif is a sequence of m positions such that at each position each character from (some subset of) the alphabet may occur with a given probability or weight. This is often described by a suitable matrix or profile, where columns correspond to positions and rows to alphabet characters. The lineage of syntactic characterizations could be ascribed to the theory of error correcting codes: a motif is a pattern w of length m and an occurrence of it is any string at a distance of d, the distance being measured in terms of errors of a certain type. For example, we can have only substitutions in a Hamming variant, substitutions and indels in a Levensthein variant, and so on. Syntactic characterizations enable us to describe the model of a motif, or a realization of it, or both, as a string or simple regular expression over an extension of the input alphabet $\Sigma$, e.g., over $\Sigma \cup \{.\}$, where "." denotes the "don't care" character.

Irrespective of the particular model or representation chosen, the tenet of motif discovery equates over-representation of a motif with surprise and hence with interest. Thus, any motif discovery algorithm must ultimately weigh motifs against some threshold, based on a score that compares empirical and expected frequency, perhaps with some normalization. The departure of a pattern w from expectation is commonly measured by so-called z-scores, which have the form:

$$z(w) = \frac{f(w) - E(w)}{N(w)} \quad (1)$$

where:
$f(w) > 0$ represents a frequency;
$E(w) > 0$ represents an expectation; and
$N(w) > 0$ is the expected value of some function of w.

For given z-score function, set of patterns W, and real positive threshold T, patterns such that $z(w) > T$ or $z(w) < -T$ are respectively dubbed over- or under-represented, or simply surprising. The problem is that the number of patterns extracted in this way may escalate quite rapidly, a circumstance that seems to preclude precisely those massive analyses that have become conceivable with the increasing availability of whole genomes. Large-scale statistical tables may not only impose an unbearable computational burden. They are also impractical to visualize and use, a circumstance that may defy the purpose of building them in the first place.

A little reflection establishes how an exponential build-up may take place. Assume that on the binary alphabet both aabaab and abbabb are asserted as reflections of candidate interesting motifs. A concise description of this motif is a.ba.b, with "." denoting the don't care, and then look for further occurrences of this motif. By this, however, the spurious patterns aababb and abbaab are also annexed.

A similar problem presents itself in the approaches that resort to the profiles or the weighted matrices previously mentioned. Even setting aside computational aspects, tables that are too large at the outset run the risk of saturating the visual bandwidth of a user. In this spirit, approaches that limit the number of patterns to be considered from the start may provide a more significant throughput, even in comparison with exhaustive methods.

SUMMARY OF THE INVENTION

In view of the foregoing and other exemplary problems, drawbacks, and disadvantages of the conventional methods and structures, an exemplary feature of the present invention is to provide methods and structures in which the significance of extensible motifs are identified by a combination of syntactic and statistical analysis.

In a first exemplary aspect of the present invention, a method of extracting extensible motifs from a sequence includes assigning a significance to extensible motifs within the sequence based upon a syntactic and statistical analysis, and identifying extensible motifs having a significance that exceeds a predetermined threshold.

In a second exemplary aspect of the present invention, a system for extracting extensible motifs from a sequence includes means for assigning a significance to extensible motifs within the sequence based upon a syntactic and statistical analysis, and means for identifying extensible motifs having a significance that exceeds a predetermined threshold.

In a third exemplary aspect of the present invention a program is embodied in a computer readable medium executable by a digital processing unit. The program includes instructions for assigning a significance to extensible motifs within the sequence based upon a syntactic and statistical analysis, and instructions for identifying extensible motifs having a significance that exceeds a predetermined threshold.

The inventors regard the motif discovery process as distributed into two stages, where the first stage unearths motifs endowed with a certain set of properties and the second filters out the interesting ones. Since the redundancy builds up in the first stage, it is there that the inventors decided to look for possible ways of reducing the unnecessary throughput. Since over-representation is measured by a score, it is desirable to find ways to neglect candidate motifs that cannot possibly make it to the top list, and ideally spot such motifs before they are even computed. Counterintuitive as it might look, the inventors discovered that such a possibility may be offered by certain attributes of "saturation" that combine in a unique way the syntactic structure and the list of occurrences or frequency for a motif.

With solid words, for example, it is known that in the worst case the number of distinct substrings in a string can be quadratic in the length of that string. Yet, if the substrings are partitioned into buckets by putting in the same bucket strings that have exactly the same set of occurrences, then only the number of buckets which are linear in the textstring are needed.

Similar linear bounds may be established for special classes of rigid motifs containing "don't cares". When combined with intervals of score monotonicity, properties of this kind support the global detection of unusual words of any length in overall linear space. Some of these conservative scoring techniques were extended recently to rigid motifs with a prescribed maximum number of mismatches or don't care.

An exemplary method and system in accordance with the present invention combines a structure of a motif pattern, as described by its syntactic specification, with a statistical measure of its occurrence count.

An exemplary embodiment of the present invention characterizes a pattern rigidly, and conjugates structure and set of occurrences. This results in a definition of motif that lends itself to a natural notion of maximality, thereby embodying statistics and structure in one measure of surprise. This is unlike all previous approaches that consider structure and statistics as separate features of a pattern.

An exemplary embodiment of the present invention provides a powerful syntactic mechanism for eliminating unimportant motifs before their score is computed. As explained above, for the class of over-represented motifs, the non-maximal motifs are not more surprising than the maximal motifs.

In an exemplary embodiment of the present invention, a combination of appropriate saturation conditions (expressed in terms of minimum number of don't cares compatible with a given list of occurrences) and the monotonicity of probabilistic scores over regions of constant frequency provide significant parsimony in the generation and testing of candidate over-represented motifs.

The advantages of exemplary embodiments of the present invention are documented by experimental results obtained when specifically targeting protein sequence families. In all cases tested, the motif reported in a database of protein families and domains known as "PROSITE" (a database of protein families and domains that includes biologically significant sites, patterns and profiles that help to reliably identify to which known protein family (if any) a new sequence belongs) as most important in terms of functional/structural relevance emerges among the top thirty extensible motifs returned by an exemplary embodiment of the present invention, often right at the top.

Of equal importance seems the fact that the sets of all surprising motifs returned in each experiment are extracted faster and come in much more manageable sizes using an exemplary embodiment of the present invention than would be obtained in the absence of saturation constraints.

An exemplary embodiment of the present invention provides a characterization of extensible motifs in the definition of which structural or syntactic properties and occurrence statistics are solidly intertwined.

An exemplary embodiment of the present invention provides a combination of saturation conditions (expressed in terms of minimum number of don't cares compatible with a given list of occurrences) and monotonicity of scores which provides significant parsimony in the generation and testing of candidate over-represented motifs.

An exemplary embodiment of the present invention isolates as candidate surprising motifs only the members of an previously well identified set of "maximally saturated" patterns. By this set being identifiable a priori, the embodiment includes motifs in the set that are known before any score is computed. By neglecting the motifs other than those in the set of "maximally saturated" patterns, surprising motifs are not overlooked. In fact, any such motif: (i) is embedded in one of the saturated motifs, and (ii) does not achieve a larger score than the latter (hence, computing its score and publishing it explicitly would take more time and space but not add information).

An exemplary embodiment of the present invention applies to extensible patterns a philosophy that was previously applied only to rigid motifs by solid words and by words of some specified fixed length affected by a specified maximum number of errors. The invention enables a transition from rigid to extensible motifs, thereby providing methods and systems that extract and weigh extensible motifs.

The inventors illustrate below the merits of exemplary embodiments of the present invention on families of protein sequences. In all cases tested, the motif reported in PROSITE as most important in terms of functional/structural relevance emerges either at the top or among the top ten or so of the output list that is provided by an exemplary embodiment of the present invention.

These and many other advantages may be achieved with the present invention.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF EXEMPLARY EMBODIMENTS OF THE INVENTION

Figure 1:
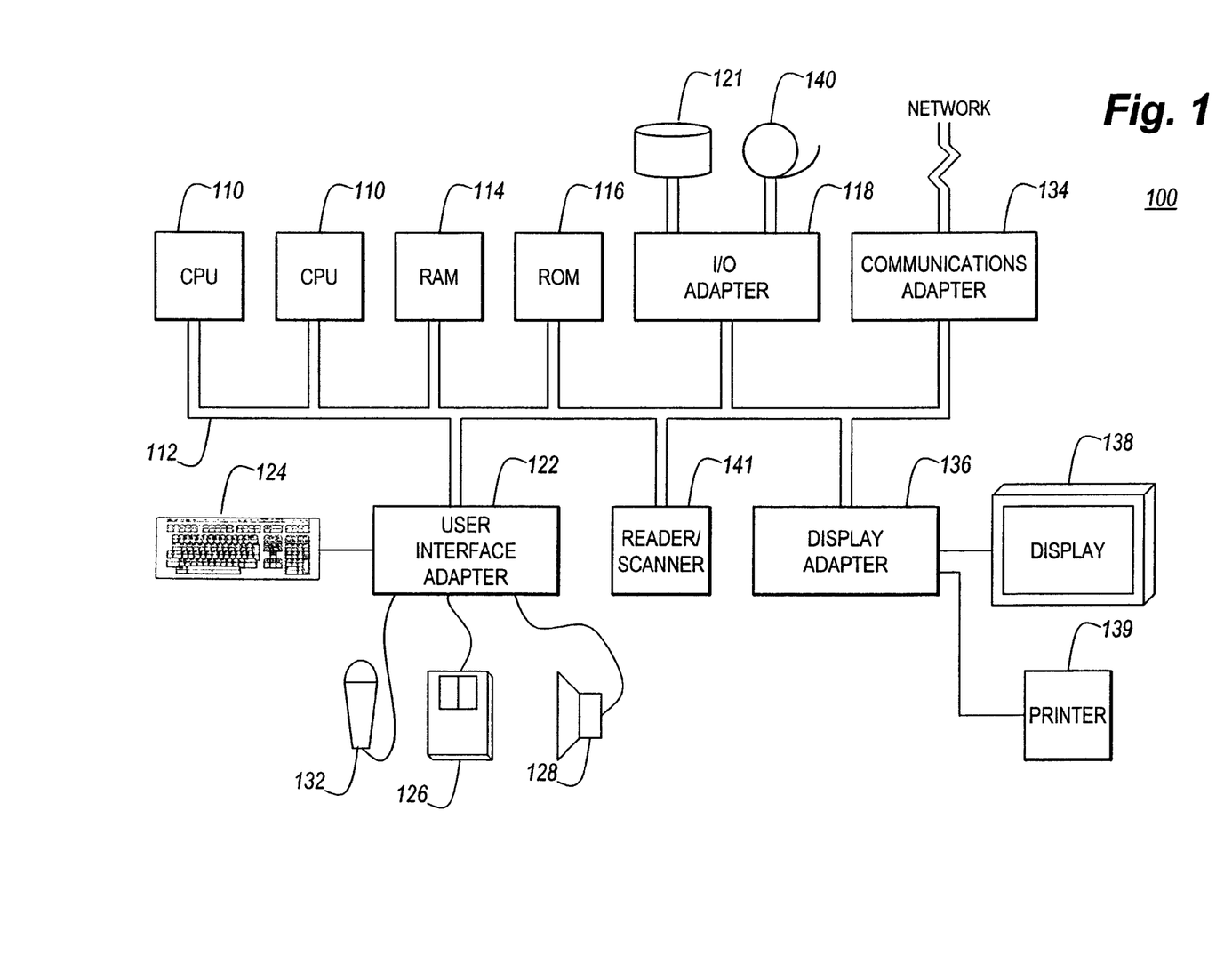
FIG. 1 illustrates an exemplary hardware/information handling system 100 for incorporating the present invention therein.
Figure 2:
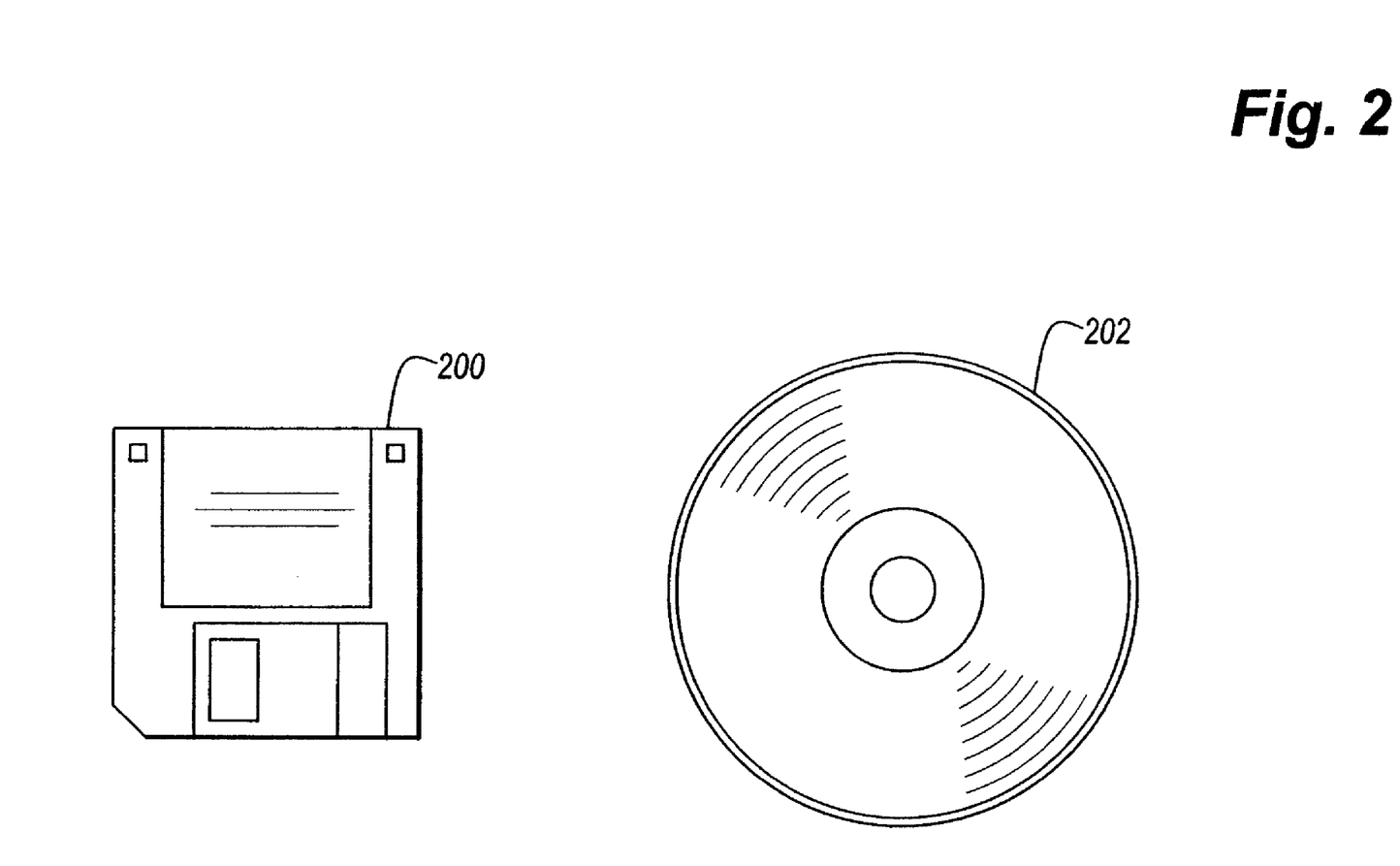
FIG. 2 illustrates a signal bearing medium 200 (e.g., storage medium) for storing steps of a program of a method according to the present invention.
Figure 3:
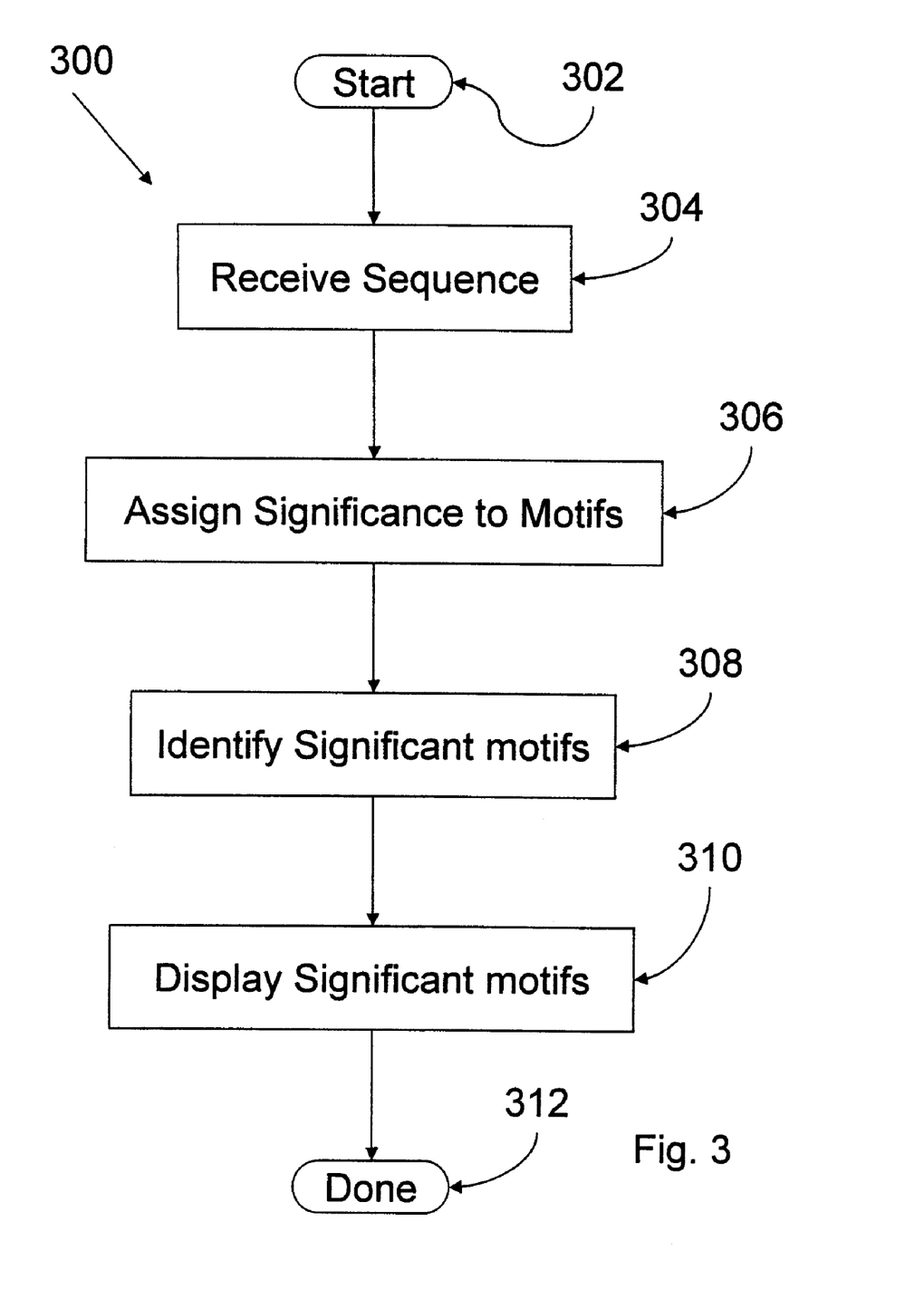
FIG. 3 illustrates a flowchart of an exemplary method in accordance with the present invention.

Referring now to the drawings, and more particularly to FIGS. 1-3, there are shown exemplary embodiments of the method and structures of the present invention.

FIG. 1 illustrates a typical hardware configuration of an information handling/computer system for use with the invention and which preferably has at least one processor or central processing unit (CPU) 111.

The CPUs 111 are interconnected via a system bus 112 to a random access memory (RAM) 114, read-only memory (ROM) 116, input/output (I/O) adapter 118 (for connecting peripheral devices such as disk units 121 and tape drives 140 to the bus 112), user interface adapter 122 (for connecting a keyboard 124, mouse 126, speaker 128, microphone 132, and/or other user interface device to the bus 112), a communication adapter 134 for connecting an information handling system to a data processing network, the Internet, an Intranet, a personal area network (PAN), etc., and a display adapter 136 for connecting the bus 112 to a display device 138 and/or printer.

In addition to the hardware/software environment described above, a different aspect of the invention includes a computer-implemented method for performing the methods described herein. As an example, an exemplary method in accordance with the present invention may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

This signal-bearing media may include, for example, a RAM contained within the CPU 111, as represented by the fast-access storage for example. Alternatively, the instructions may be contained in another signal-bearing media, such as a magnetic data storage diskette 200 (FIG. 2), directly or indirectly accessible by the CPU 111.

Whether contained in the diskette 200, the computer/CPU 111, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, compiled from a language such as "C", etc.

To proceed with a formal definition of the concepts highlighted above, let s be a sequence of sets of characters from an alphabet $\Sigma \cup \{.\}$, where '.'$\notin \Sigma$ denotes a don't-care (dot, for short) and the rest are solid characters. The inventors use $\sigma$ to denote a singleton character or a subset of $\Sigma$. For character (sets) $e_1$ and $e_2$, the inventors write $e_1 < e_2$ if and only if $e_1$ is a dot or $e_1 \subset e_2$. Allowing for spacers in a string is what makes it extensible. Such spacers are indicated by annotating the dot characters. Specifically, an annotated "." character is written as $.^\alpha$ where $\alpha$ is a set of positive integers $\{\alpha_1, \alpha_2, \ldots, \alpha_k\}$ or an interval $\alpha = [\alpha_1, \alpha_u]$, representing all integers between $\alpha_1$ and $\alpha_u$ including $\alpha_1$ and $\alpha_u$. Whenever defined, d will denote the maximum number of consecutive dots allowed in a string. In such cases, for clarity of notation, the inventors use the extensible wild card denoted by the dash symbol "-" instead of the annotated dot character, $.^{[1,d]}$ in the string. Note that '-'$\notin \Sigma$. Thus a string of the form $a.^{[1,d]}$ will be simply written as a-b.

A motif m is extensible if it contains at least one annotated dot, otherwise m is rigid. Given an extensible string m, a rigid string m' is a realization of m if each annotated dot $.^\alpha$ is replaced by $l \in \alpha$ a dots. The collection of all such rigid realizations of m is denoted by R(m). A rigid string m occurs at position l on s if $m[j] < s[l+j-1]$ holds for $1 \le j \le |m|$. An extensible string m occurs at position l in s if there exists a realization m' of m that occurs at l. Note than an extensible string m could possibly occur a multiple number of times at a location on a sequence s.

For a sequence s and positive integer k, $k \le |s|$, a string (extensible or rigid) m is a motif of s with $|m| > 1$ and location list $L_m = (l_1, l_2, \ldots, l_p)$, if both m[1] and m[|m|] are solid and $L_m$ is the list of at all and only the occurrences of m in s. Given a motif m let $m[j_1], m[j_2], \ldots m[j_l]$ be the l solid elements in the motif m. Then the sub-motifs of m are given as follows: for every $j_i, j_t$ the sub-motif $m[j_i \ldots j_t]$ is obtained by dropping all the elements before (to the left of) $j_i$ and all elements after (to the right of) $j_t$ in m. The inventors also note that m is a condensation for any of its sub-motifs. The inventors are interested in motifs for which any condensation would disrupt the list of occurrences. Formally, let $m_1, m_2, \ldots, m_k$ be the motifs in a string s. A motif $m_i$ is maximal in length if there exists no $m_j$, $l \ne i$ with $|L_{m_i}| = |L_{m_j}|$ and $m_i$ is a sub-motif of $m_j$. A motif $m_i$ is maximal in composition if no dot character of $m_i$ can be replaced by a solid character that appears in all the locations in $L_{m_i}$. A motif $m_i$ is maximal in extension if no annotated dot character of $m_i$ can be replaced by a fixed length substring (without annotated dot characters) that appears in all the locations in $L_{m_i}$. A maximal motif is maximal in composition, in extension and in length.

Expectations and Scores

Beginning by deriving some simple expressions for the probability $p_m$ of an extensible motif m under stationary, iid assumptions. Let m be an extensible motif generated by a stationary, i.i.d. source which emits $\sigma \in \Sigma$ with probability $p_\sigma$. Consider the set R(m) of all possible realizations of m. Each realization is a string over $\Sigma \cup \{.\}$. For a specific realization $\overline{m}$, its probability $p_{\overline{m}}$ is given by:

$$p_{\overline{m}} = \prod_{\sigma \in \Sigma} (p_\sigma)^{j_\sigma}, \qquad (2)$$

where:

$j_\sigma$ is the number of times $\sigma$ appears in $\overline{m}$.

Thus, the dot has implicitly probability 1.

An extensible motif is degenerate if it can possibly have multiple occurrences at a site i on the input s.

Lemma 1 Let m be an extensible non-degenerate motif generated by a stationary, iid source which emits ($\sigma \in \Sigma$) with probability $p_\sigma$. Let $j_\sigma$ be the number of times $\sigma$ appears in m and let e be the number of annotated dots in m with annotations $\alpha_1, \alpha_2, \ldots \alpha_e$. Then $$p_m = \prod_{\sigma \in \Sigma} (p_\sigma)^{j_\sigma} \prod_{i=1}^{e} |\alpha_i| \qquad (3)$$

Proof. Since the motif is non-degenerate, by the definition of realization of a motif, $$p_m = \sum_{\overline{m} \in R(m)} (p_{\overline{m}}) \qquad (4)$$

Hence we need to compute $p_{\bar{m}}$ where $\bar{m}$ is a rigid motif. Assume $\bar{m}$ is a rigid motif with no dot characters. By the i.i.d. assumption:

$$p_{\bar{m}} = \Pi_{\sigma \in \Sigma}(p_\sigma)^{j_\sigma} \qquad (5)$$

Next, consider $\bar{m}$ to be a rigid motif with possibly some dot characters. Again, clearly:

$$p_{\bar{m}} = \Pi_{\sigma \in \Sigma}(p_\sigma)^{j_\sigma} \qquad (6)$$

In other words, only the solid characters contribute non-trivially to the computation of $p_{\bar{m}}$. Hence, if m is not rigid:

$$p_m = |R(m)| \prod_{\sigma \in \Sigma} (p_\sigma)^{j_\sigma} \qquad (7)$$

But $$|R(m)| = \prod_{i=1}^{e} |\alpha_i| \qquad (8)$$

hence the result.

Corollary 2 If m is a non-degenerate extensible motif where each m[i] is a set of (homologous) characters, then $$p_m = \prod_{m[i] \neq '.', '\_'} \left( \sum_{\sigma \in m[i]} p_\sigma \right) \prod_{i=1}^{e} |\alpha_i| \qquad (9)$$

Let $M^s$ denote a set of strings that has only the solid characters of at least s occurrences of m. For example, consider the motif a-b with realizations a.b, a..b and a...b. Then:

$$M^1 = \{a.b, a..b, a...b\} \qquad (10)$$

since m occurs once on each $m \in M^1$ $$M^2 = \{a.bb, a..bb, a.b.b\} \qquad (11)$$

since m occurs twice on each $m \in M^2$:

$$M^3 = \{a.bbb\} \qquad (12)$$

since m occurs three times on $m \in M^3$.

Corollary 3 Let m be a degenerate (possibly with multiple occurrences at a site) extensible motif, and let:

$$p_{m^k} = \sum_{m' \in M^{k+1}} p_{m'} \qquad (13)$$

then $$p_m = \sum_{k=0}^{r-1} (-1)^k (p_{m^{k+1}}) \qquad (14)$$

This follows directly from the inclusion-exclusion principle.

Notice that for a degenerate motif, Equation (2) is the zero-th order approximation of Equation (13). The first order approximation is:

$$p_m \approx p_m{}^1 - p_m{}^2 \qquad (15)$$

and the second order approximation is $$p_m \approx p_m{}^1 - p_m{}^2 + p_m{}^3 \qquad (16)$$

and so on. Using Bonferroni's inequalities, a k th order approximation of $p_m$ is an over-estimate of $p_m$, if k is odd.

Next, the form of $p_m$ for a non-degenerate motif when input m is assumed to be generated by a Markov chain is obtained. For the derivation below, we assume the Markov chain has order 1. For further discussion, we introduce the following definition.

Definition 4 (cell $<\sigma_1, \sigma_2, l>$, $C(m)$) A substring $\hat{m}$, on m is a cell, that begins and ends in solid characters with only non-solid intervening characters: $\sigma_1$, at the start and $\sigma_2$ at the end position and l is the number of intervening un-annotated dot characters. If the intervening character is the extensible character, then l takes a value of −1. For convenience, the cell is represented by the triplet $<\sigma_1, \sigma_2, l>$. $C(m)$ is the collection of all such cells of m.

For example, $$C(ab..c.d-g) = \{<a,b,0>, <b,c,2>, <c,d,1>, <d,g,-1>\} \qquad (17)$$

Let $$p_{\sigma_1, \sigma_2}^{(k)}$$

denote the probability of moving from $\sigma_1$ to $\sigma_2$ in k steps. Let s be a stationary, irreducible, aperiodic Markov chain of order 1 with state space $\Sigma$ ($|\Sigma| \infty$). Further, $\pi_\sigma$ is the equilibrium probability of $\sigma \in \Sigma$ and the ($|\Sigma| \times |\Sigma|$) transition probability matrix $P[i,j]$ is defined as $$p_{\sigma_i, \sigma_j}^{(1)}.$$

For a rigid motif $\bar{m}$, for each cell $<\sigma_1, \sigma_2, l> \in C(\bar{m})$ is such that $l \geq 0$. It is easy to see that when $l \geq 0$, the cell represents the (l+1)-step transition probability given by $P^{l+1}$, i.e.,:

$$p_{\sigma_1(.)l \sigma_2} = P^l[\sigma_1, \sigma_2]. \qquad (18)$$

Thus for a rigid motif $\bar{m}$, $$p_{\bar{m}} = \pi_{\bar{m}[1]} \prod_{<\sigma_1, \sigma_2, l> \in C(m)} P^l[\sigma_1, \sigma_2]. \qquad (19)$$

From now on, let u and v be two motifs such that v is a condensation of u, and consider an arbitrary sequence of consecutive unit expansions—consisting each of inserting a character or character set at some position, or replacing a dot character with a solid character or character set—that transforms u into v. A score z is monotonic for u and v if the value of z is always either increasing or decreasing over any such expansion. The key observation here is that, under most probabilistic settings, the probability of a condensation v of u obeys $p_v \leq p_u$. This is almost immediate under iid distribution, as the following claim shows.

Theorem 5 Let v and u be possibly degenerate extensible motifs under the iid model and let v be a condensation of u. Then, there is an integer $\hat{p} \leq 1$ such that:

$$p_v = p_u \hat{p}. \qquad (20)$$

Proof: It is enough to consider the case of a unit condensation, i.e., where v has one more solid character than u. The claim holds trivially when the extra character is introduced as a prefix, an infix, or a suffix of u. In fact, in any such case the probability of the extra character multiplies each term of Equation (6), whence the whole probability as well.

Consider next the case where the solid character in v substitutes a don't care of u. We begin by describing an alternate way to compute $p_u$. With l denoting the length of a longest string in R(u), compute the set of all strings over $\Sigma^l$ and store them consecutively row-wise in a table. Compute, for each row, the probability of the string in that row, which is the product of the probabilities of the individual characters (the sum of all row probabilities is 1). Consider now the realizations in R(u) in succession. Check each realization against every row of the table; wherever the two match, mark the row if it had not been already marked. Let R be the set of rows that are marked at the outset. Clearly, adding up the probabilities of the rows in R yields $p_u$. Consider now the set of rows that would be similarly involved in the computation of $p_v$. This must be a subset of R, whence $p_v \leq p_u$.

With Markov processes, the intuition at the basis is that if we split the transition probability into two consecutive segments then we have:

$$P^l[\sigma_1, \sigma_2] = \Sigma_{\sigma_k \in \Sigma} P^{l_1}[\sigma_1, \sigma_k] \times P^{l_2}[\sigma_k, \sigma_2] \tag{21}$$

where:

$$l = l_1 + l_2. \tag{22}$$

Since all:

$$P^l[\sigma_i, \sigma_j] \leq 0 \tag{23}$$

then any specific character (or alphabet subset) acting as a bottleneck yields:

$$P^l[\sigma_1, \sigma_2] \leq P^{l_1}[\sigma_1, \sigma_k] \times P^{l_2}[\sigma_k, \sigma_2]. \tag{24}$$

Theorem 6 If:

$$f(u) = f(v) > 0 \tag{25}$$

$$N(v) < N(u), \tag{26}$$

and $$E(v)/N(wv) \leq E(u)/N(u), \tag{27}$$

then $$\frac{f(v) - E(v)}{N(v)} > \frac{f(u) - E(u)}{N(u)} \tag{28}$$

Proof. Multiplying both terms by N(v)/E(v) and using the assumption:

$$f(v) = f(u) \geq 0 \tag{29}$$

we get, after rearrangement:

$$\frac{f(u)}{E(v)}\left(1 - \frac{N(v)}{N(u)}\right) > 1 - \frac{E(u)N(v)}{E(v)N(u)} \tag{30}$$

Since:

$$0 < N(v)/N(u) < 1 \tag{31}$$

then the left hand side is always positive. The right hand size is always negative or zero.

When N(u) is the square root of the variance, the z-score takes up the form:

$$z(u) = \frac{f(u) - E(u)}{\sqrt{\text{Var}(u)}} \tag{32}$$

In the Bernoulli model, for instance, this variance results in $\sqrt{np_u(1-p_u)}$. Let $p_m$ be the probability of the motif m occurring at any location i on the input string s with n=|s| and let $k_m$ be the observed number of times it occurs on s. When it can be assumed that the occurrence of a motif m at a site is an i.i.d process, for large n and $k_m \ll n$ we have:

$$\frac{k_m - np_m}{\sqrt{np_m(1 - p_m)}} \to N(0, 1) \tag{33}$$

Theorem 7 Let u and v be motifs generated with respective probabilities $p_u$ and:

$$p_v = p_u \hat{p} \tag{34}$$

according to an iid process. If f (u)=f (v) and $p_u < \frac{1}{2}$ then:

$$\frac{f(v) - E(v)}{\sqrt{E(v)(1 - p_v)}} > \frac{f(u) - E(u)}{\sqrt{E(u)(1 - p_u)}} \tag{35}$$

Proof. The functions:

$$N(u) = \sqrt{E(u)(1 - p_u)} \tag{36}$$

and E(u)/N(u) satisfy the conditions of Theorem 6. First, E(v)<E(u). Indeed, since:

$$|v| - |u|/(n - |u| + 1) > 0, \tag{37}$$

$$\frac{E(v)}{E(u)} = \frac{(n - |v| + 1)p_v}{(n - |u| + 1)p_u} = \left(1 - \frac{|v| - |u|}{n - |u| + 1}\right)\hat{p} < \hat{p} < 1. \tag{38}$$

Next, we study the ratio:

$$\left(\frac{N(v)}{N(u)}\right)^2 = \left(1 - \frac{|v| - |u|}{n - |u| + 1}\right)\frac{p_v(1 - p_v)}{p_u(1 - p_u)} < \frac{p_v(1 - p_v)}{p_u(1 - p_u)} \tag{39}$$

The concave product $p_u(1-p_u)$ reaches its maximum for $p_u = \frac{1}{2}$. Since we assume $p_u < \frac{1}{2}$, the rightmost term is smaller than one. The monotonicity of N(u) is satisfied.

Finally, we prove that also E(u)/N(u) is monotonic, i.e., that:

$$E(v)/N(v) \leq E(u)/N(u), \tag{40}$$

which is equivalent to:

$$\frac{E(v)}{E(u)} \frac{1 - p_u}{1 - p_v} \leq 1 \tag{41}$$

but E(v)/E(u)<1 by hypothesis and $(1-p_u)/(1-p_v)<1$ since $p_u > p_v$.

In conclusion, an exemplary embodiment of the present invention may restrict the z-score computation to classes of maximal motifs, i.e., only compute the z-score for the maximally saturated motif among those in each class of motifs sharing the same list of occurrences.

An exemplary embodiment of the present invention pairwise iterates combinations of segments of maximal extensible motifs, and prunes those pairings that are found to not be viable. The input may be a string s of size n and two positive integers, K and D. The extensibility parameter D is interpreted in the sense that up to D (or 1 to D) number of dot characters between two consecutive solid characters are allowed. The output is all maximal extensible (with D spacers) patterns that occur at least K times in s.

Incidentally, an exemplary embodiment of the present invention may extract rigid motifs as a special case. For this, it suffices to interpret D as the maximum number of dot characters between two consecutive solid characters.

An exemplary embodiment converts the input into a sequence of possibly overlapping cells (see Definition 4). A maximal extensible pattern is a sequence of cells.

Initialization Phase

The cell is the smallest extensible component of a maximal pattern and the string can be viewed as a sequence of overlapping cells. If no don't care characters are allowed in the motifs then the cells are non-overlapping. An initialization phase in accordance with an exemplary embodiment of the present invention may:

1) Construct patterns that have exactly two solid characters in them and separated by no more than D spaces or "." characters. This may be done by scanning the string s from left to right.

Further, for each location this exemplary embodiment may store start and end positions of the pattern. For example, if s=abzdabyxd and K=2, D=2, then all the patterns generated at this step are: ab, a.z, a..d, bz, b.d, b..a, zd, z.a, z..b, da, d.b, d..y, a.y, a..x, by, b.x, b..d, yx, y.d, xd, each with its occurrence list. Thus $L_{ab}=\{(1,2),(5,6)\}$, $L_{a.z}=\{(1,3)\}$ and so on.

2) The extensible cells may be constructed by combining all the cells with a dot character and the same start and end solid characters. The location list is updated to reflect the start and end position of each occurrence. Continuing the previous example, b—d is generated at this step with $L_{b-d}=\{(2,4),(6,9)\}$. All cells m with $|L_m|<K$ are discarded. In the example, the only surviving cells are ab, b—d with $$L_{ab}=\{(1,2),(5,6)\} \text{ and } L_{b-d}=\{(2,4),(6,9)\}$$

An exemplary embodiment of the present invention may also have an iteration phase. Let B be the collection of cells. If m=Extract(B), then m∈B and there does not exist m'∈B such that m'>m holds: $m_1>m_2$ if one of the following holds: (1) $m_1$ has only solid characters and $m_2$ has at least one non-solid character (2) $m_2$ has the "—" character and $m_1$ does not, and, (3) $m_1$ and $m_2$ have $d_1,d_2>0$ dot characters respectively and $d_1<d_2$.

Further, $m_1$ is ~-compatible with $m_2$ if the last solid character of $m_1$ is the same as the first solid character of $m_2$.

Further if $m_1$ is ~-compatible with $m_2$, then $m=m_1\sim m_2$ is the concatenation of $m_1$ and $m_2$ with an overlap at the common end and start character and:

$$L'_m=\{((x,y),z)|((x,l),z)\in L'_{m_1},((l,y),z)\in L'_{m_2}\}. \quad (42)$$

For example if $m_1$=ab and $m_2$=b.d then $m_1$ is ~-compatible with $m_2$ and $m_1\sim m_2$=ab.d. However, $m_2$ is not ~-compatible with $m_1$.

An example, of this procedure is described by the pseudo-code shown below. NodeInconsistent(m) is a routine that checks if the new motif m is non-maximal w.r.t. earlier non-ancestral nodes by checking the location lists. Steps G: 18-19 detect the suffix motifs of already detected maximal motifs. Result is the collection of all the maximal extensible patterns.

Main( )
Result←{ };
B←{$m_i$|$m_i$ isacell};
For each m=Extract(B)
Iterate(m,B,Result);
Iterate(m,B,Result)

G:1 m'←m;
G:2 For each b=Extract(B) with
G:3 ((b~—compatible m) OR (m'~—compatible b))
G:4 If (m'~—compatible b)
G:5 $m_t$←m'~b;
G:6 If NodeInconsistent($m_t$) exit;
G:7 If ($|L_m|=|L_b|$)B←B−{b};
G:8 If($|L_m|\geq K$)
G:9 m'←$m_t$;
G:10 Iterate(m',B,Result);
G:11 If (b~—compatible m)
G:12 $m_t$←b~m';
G:13 If NodeInconsistent($m_t$) exit;
G:14 If ($|L_m|=|L_b|$) B←B−{b};
G:15 If ($|L_m|\geq K$)
G:16 m'←$m_t$;
G:17 Iterate(m',B,Result);
G:18 For each r∈Result with $L_r=L_{m'}$
G:19 If (m' is not maximal w.r.t. r) return;
G:20 Result←Result∪{m'};

Correctness follows from the observation that the above exemplary procedure essentially constructs the inexact suffix tree of implicitly, in a different order. A tight time complexity is more difficult to come by, however, if we consider M to be the number of extensible maximal motifs and S to be the size of the output—i.e. the sum of the sizes of the motifs and the sizes of the corresponding location lists—then the time taken by an exemplary embodiment of the present invention is O(SM log M). In experiments by the inventors of the kind described below, at 3 GHz clock, processing time ranged typically from few minutes to half an hour.

A detailed description of an implementation of one exemplary embodiment in accordance with the present invention follows.

Since a pattern space can vary dramatically for different classes of inputs, a number of parameters have been introduced to allow a user maximally exploit his specific domain knowledge. One way of viewing this control is to prune the pattern space appropriately and various parameters are specified to meet this objective. There are essentially two classes of pruning parameters: (1) combinatorial and (2) statistical. To avoid clutter, we describe only a few of the pruning parameters here. Each parameter has a default value and it is not mandatory to specify them all.

Combinatorial Pruning

1. Pruning by Occurrences:
    a. -k<Num>: Num is the quorum or the minimum number of times a pattern must occur in the input.
    b. -c: When this is specified the quorum k is in terms of the number of sequences where the pattern occurs at least once. For example, if this option is set and further -k10 is specified, then a valid pattern must occur in at least 10 distinct sequences. However if this option is not set then a valid pattern must have at least 10 occurrences, not necessarily in distinct sequences.
2. Pruning by Composition:
    a. Using homology groups:
        (1) -b<File>: File lists the symbol equivalences that define the homology groups. The default file is an empty file.
        (2) -n<Num>: Num is the maximum number of bracketed elements (equivalence classes) in a pattern. For example, if "-n2" is specified, then [IL]...[LV], L.[LV]-V are valid patterns but not [LV][IL][LV]..L.
    b. -R: When this mode is specified, only rigid patterns are discovered.

c. Extensibility: The following two parameters may be used to prune the space of extensible patterns. FIG. 1 shows an example of the size of the pattern space for different parameter values.

(1) -D<Num>: Num is the maximum number of consecutive don't care characters ('.') in the realization of an extensible pattern. Note that a don't care character and an extensible character are never consecutive in any valid pattern. For example, if "-D3" is specified, then L...V, LV, L.L.V are valid patterns but not L....L. Further, an extensible pattern of the form L-V implies that there are one to three don't care characters in the occurrences of this pattern between the bases L and V.

(2) -d<Num>: Num is the minimum number of non-extensible characters (including the don't care character) between two consecutive extensible characters ('-'). For example, if "-d4" is specified, then L..H-L.H-L is a valid pattern but not L...H-L.H-L.

Statistical Pruning

1. -p<File>: File lists the symbol probabilities used for the probabilistic analysis.

2. -z<Val>: Val is the minimum absolute value of Z-score of the patterns.

Information Display

1. Displaying occurrence information: The different modes of displaying the occurrence list of each valid pattern may be as follows. (1) The occurrence list is not displayed (option -L0). (2) Only the start position of each occurrence is displayed (option -L1). (3) The start and end position of each occurrence is displayed as $x_1$-$x_2$ where $x_1$ is the starting position and $x_2$ the end position(option -L4).

2. Displaying statistical information: The different statistical information displayed for possible use are (1) the probability of occurrence of a pattern, (2) the observed number of occurrences, and (3) the Z-score. Table 1 shows an example.

TABLE 1

Numbers of patterns in the experiment in Table 8 with Z-Score ≧100.0 at various values of parameters D and d with quorum k = 53

|   | | D | | | |
|---|---|---|---|---|---|
|   |   | 2 | 3 | 4 | 5 |
| d | 3 | 121 | 196 | 370 | 1145 |
|   | 4 | 121 | 194 | 355 | 1008 |
|   | 5 | 114 | 182 | 326 | 891 |
|   | 8 | 112 | 178 | 313 | 758 |
|   | 10 | 112 | 178 | 313 | 727 |

TABLE 2

A statistical summary of a small set of valid patterns on the Coagulation factors 5/8 type C domain, also used in Table 8.

| Pattern | Probability | Occ. | Z-Score |
|---|---|---|---|
| [LIVP]-[LM]R.[GE][LIVP].GC | 2.05647e−07 | 57 | 585.494 |
| LR.[GE][LIVP].GC | 2.53136e−07 | 63 | 582.758 |
| L..[GE][LIVP].GC | 4.77614e−06 | 70 | 148.626 |
| R-[GE][LIVP].GC | 6.33367e−06 | 66 | 121.48 |
| L-[GE][LIVP].GC | 1.43284e−05 | 83 | 101.21 |
| G[LIVP][GE].GC | 3.98344e−05 | 77 | 55.359 |
| R-[LIVP].GC | 4.68467e−05 | 65 | 42.6968 |
| L-[LIVP].GC | 0.00010598 | 112 | 48.3873 |

FIG. 3 illustrates a flowchart 300 of an exemplary method in accordance with the present invention. The flowchart 300 starts at step 302 and continues to step 304, where the method receives a sequence. The flowchart continues to step 306, where the method assigns a significance to an extensible motif within the sequence based upon a combination of syntactic and statistical analysis, an example of which is described above. The method continues to step 308 where the method identifies a significant extensible motif by, for example, determining whether the significance assigned to an extensible motif exceeds a predetermined threshold. The method continues to step 310 where the system displays a list of the identified extensible motif from the sequence and continues to step 312 where the method ends.

EXPERIMENTAL RESULTS

The inventors tested an exemplary embodiment in accordance with the present invention on six protein families by seeking the surprising motifs in each. Each family was picked at random from the PROSITE database.

High potential iron-sulfur proteins (HiPIP) (PROSITE I.D. PS00596). This is a specific class of high-redox potential 4Fe-4S ferredoxins that function in anaerobic electron transport and which occur in photosynthetic bacteria and in Paracoccus denitrificans. Two of the cysteine residues of the motif shown in Table 3 are involved in binding to the iron-sulfur cluster. This is the top-ranking motif discovered by the exemplary embodiment out of the possible 273 extensible motifs.

Streptomyces subtilisin-type inhibitors (PROSITE I.D PS00999). Bacteria of the Streptomyces family produce a family of proteinase inhibitors characterized by their strong activity toward subtilisin. They are collectively known as SSI's: Streptomyces Subtilisin Inhibitors. The exemplary embodiment discovers this functionally significant motif as the top ranking one out of 470 extensible motifs (Table 4).

Nickel-dependent hydrogenases (PROSITE I.D PS00508). These are enzymes that catalyze the reversible activation of hydrogen and are further involved in the binding of nickel. Again, this functionally significant motif is detected in the top three by the exemplary embodiment out of 4150 extensible motifs (Table 5).

G-protein coupled receptors family 3 (PROSITE I.D PS00980). The exemplary embodiment finds that the most important structural motif in this family is in the top thirty of the motifs out of 3508 extensible motifs (Table 6).

Chitin-binding type-1 domain (PROSITE I.D PS00026). The exemplary embodiment finds that the most important structural motif in this family is in the top two of the motifs out of 886 extensible motifs (Table 7).

Coagulation factors 5/8 type C domain (FA58C) (PROSITE I.D PS01286). The exemplary embodiment finds that the most important structural and functional motif in this family is in the top two of the motifs out of 80290 extensible motifs (Table 8).

To summarize, the inventors discovered that in almost all cases, the motif documented as the most important (as functionally/structurally relevant motif) in PROSITE is in the top extensible motifs returned by the exemplary embodiment as surprising. In the fourth set (Table 6) the inventors find the PROSITE motif at position 42, this experiment shows that in some particular cases the patterns reported by the exemplary embodiment can be grouped together, in fact the top scoring motifs are very close to each other in location and composition. This reveals that a post-processing step that clusters together the top patterns may improve the results. In all cases, the difference in the z-score between the top few and the rest is dramatic as can be seen in Tables 3 to 8. The differing values of the Z-scores of each family are attributed to the different sizes of the families (the number of members and the length of each member).

The inventors also tested the sensitivity and selectivity of an exemplary embodiment of the present invention using the families as reported in PROSITE. The following six sets were selected by the inventors randomly in each family: 5 sequences in each of the families, high potential iron-sulfur proteins, streptomyces subtilisin-type inhibitors, nickel-dependent hydrogenases, g-protein coupled receptors family 3 and coagulation factors 5/8 type C domain, and 8 sequences from the family of chitin-binding type-1 domain.

First each family was contaminated with one of the sets that was drawn from a different family (for example the five sequences of G-protein was mixed with the family of the hydrogenases). Next, the inventors contaminated each family with two sets from a different family and then subsequently three sets. In each of the experiments the inventors discovered that the top ranked motifs were exactly as reported in Tables 3 to 8.

TABLE 3

The functionally relevant motif is shown in bold for high potential iron-sulfur proteins (HiPIP) (id PS00596). Here 22 sequences of about 2500 bases were analyzed at $k = 22$, $D = 9$, $d = 4$.

| Rank | z-score | Motif |
| --- | --- | --- |
| 1 | 1497.62 | C-(6,7,8,9)[LIVM]...G[YW]C..[FYW] |
| 2 | 978.872 | P-(3,4,6,8,9)[LIVM]...G[YW]C..[FYW] |
| 3 | 590.866 | C-(6,7,8,9)[LIVM]...G[YW]C-(1,3,4,5,6,7)A |
| 4 | 564.821 | C-(6,7,8,9)[LIVM]...G[YW]C-(1,3,4,5,6,7)[ATD] |
| 5 | 537.73 | [LIVM]-(1,2,3,4,5,7,8,9)G[YW]C..[FYW] |
| 6 | 385.2 | [LIVM]-(1,2,3,4,5,7,8,9)G[FYW]C..[FYW] |
| 7 | 161.173 | [LIVM]...G[FYW]C-(2,4)[FYW] |
| 8 | 156.184 | [LIVM]-(1,2,3,4,5,6,7,8,9)G[YW]C |
| 9 | 138.881 | [LIVM]-(1,3,4,5,6)[LIVM]...G[FYW]C-(1,3,4,5,6,7)A |

TABLE 4

The functionally relevant motif is shown in bold for Streptomyces subtilisin-type inhibitors signature (id PS00999). Here 20 sequences of about 2500 bases were analyzed at $k = 20$, $D = 4$, $d = 4$.

| Rank | z-score | Motif |
| --- | --- | --- |
| 1 | 7.60E+07 | RA.T[LV].C.P-(2,3)G.HP....AC[ATD].L.....[ASG] |
| 2 | 21416.8 | A..[LV].C.P-(2,3)G.HP-(1,2,4)[ASG].[ATD] |
| 3 | 8105.33 | A-(1,4)T....P-(2,3)G.HP....[ATD]-(3)L....[ASG] |
| 4 | 5841.85 | [ATD].T....P-(1,2,3)G.HP-(1,2,4)A.[ATD] |
| 5 | 4707.62 | P.[ASG]-(2,3,4)P....AC[ATD].L.....[ASG] |
| 6 | 4409.21 | A..[LV]...P-(2,3)G.HP-(1,2,4)A.[ATD] |
| 7 | 3086.17 | P-(1,2,3)[ASG]..P-(4)AC[ATD].L.....[ASG] |
| 8 | 3068.18 | R..[ATD]....P-(2,3)G.HP-(1,2,4)[ASG].[ATD] |
| 9 | 2615.98 | [ASG][ATD]-(1,3,4)P....AC[ATD].L.....[ASG] |
| 10 | 2569.66 | [ASG]-(1,2,3,4)P....AC[ATD].L.....[ASG] |
| 11 | 2145.6 | G-(2,3)P....AC[ATD].L.....[ASG] |

TABLE 5

The functionally relevant motifs are shown in bold for Nickel-dependent hydrogenates (PROSITE I.D. PS00508). Here 22 sequences of about 23000 bases were analyzed at $k = 22$, $D = 4$, $d = 3$.

| Rank | z-score | Motif |
| --- | --- | --- |
| 1 | 295840 | [LIM]-(1,2,3,4)[STA][FY]DPC[LIM][ASG]C[ASG].H |
| 2 | 2.86E+05 | [LIM]-(1,2,3,4)[ASG][FY]DPC[LIM][ASG]C[ASG].H |
| 3 | 155736 | R-(1,4)[FY]DPC[LIM][ASG]C[ASG].H |
| 4 | 78829 | [LIM]-(1,2,3,4)[STA].DPC[LIM][ASG]C[ASG].H |
| 5 | 76101.9 | [LIM]-(1,2,3,4)[ASG].DPC[LIM][ASG]C[ASG].H |
| 6 | 34205.6 | [STA]-(1,4)DPC[LIM][ASG]C[ASG].H |
| 7 | 30325.1 | [LIM]-(1,2,3,4)[STA][FY]D.C[LIM][ASG]C..H |
| 8 | 29276 | [LIM]-(1,2,3,4)[ASG][FY]D.C[LIM][ASG]C..H |
| 9 | 20527.3 | [ASG]-(1,4)DPC[LIM][ASG]C[ASG].H |
| 10 | 17503.4 | [LIM]-(1,2,3,4)[ASG]..PC[LIM][ASG]C[ASG].H |

TABLE 6

The functionally relevant motif is shown in bold for G-protein coupled receptors family 3 (PROSITE I.D. PS00980). This run involved 25 sequences of about 25000 bases each at $k = 25$, $D = 4$, $d = 8$.

| Rank | z-score | Motif |
| --- | --- | --- |
| 1 | 2.84E+09 | Y...L....C..[FYW]A..[STAH]R..P..FNE[STAH]K.I.F[STAH]M |
| 2 | 8.28E+07 | V-(1,3,4)G...S..[STAH]....N...L....Q-(4)[STAH]....L.[DN]...[FYW]..F....P....Q..A...I |
| 3 | 5.55E+07 | L-(2,3)F...Q....[STAH][STAH]....L.[DN]...[FYW]..F.R..P.D..Q..A...I |
| 4 | 4.27E+07 | L-(2,3)F...Q.[STAH]..[STAH][STAH].....S....[FYW]..F.R..P.D..Q..A...I |
| 5 | 4.23E+07 | L....I...[STAH]..[STAH]....LS[DN]...[FYW]..F.R..P.D..Q..A...I |
| 6 | 3.99E+07 | LF-(3)Q....[STAH][STAH]....S[DN]...[FYW]..F.R..P.D..Q..A...I |
| 7 | 3.38E+07 | LF-(3)Q....[STAH][STAH]....L.[DN]...[FYW]..F.R..P.D..Q..A...I |
| 8 | 3.38E+07 | LF...Q....[STAH]-(4)L.[DN]...[FYW]..F.R..P.D..Q[STAH].A...I |
| 9 | 3.29E+07 | I-(1)Q.[STAH]..[STAH]....LS[DN]...[FYW]..F.R..P.D..Q..A...I |
| 10 | 3.29E+07 | I.Q-(4)[STAH]....LS[DN]...[FYW]..F.R..P.D..Q[STAH].A...I |
| 11 | 3.29E+07 | I.Q.[STAH]..[STAH]-(4)LS[DN]...[FYW]..F.R..P.D..Q..A...I |
| 12 | 3.10E+07 | L....Q-(1,4)[STAH]..[STAH]....LS[DN]...[FYW]..F.R..P.D..Q..A...I |
| 13 | 2.77E+07 | L[FYW]-(3)Q.[STAH]..[STAH]....LS....[FYW]..F.R..P.D..Q..A...I |
| 14 | 2.58E+07 | L-(4)Q.[STAH]..[STAH]....LS[DN]...[FYW]..F.R..P.D..Q..A...I |
| 15 | 2.30E+07 | S.[STAH]S-(2,4)LS[DN]...[FYW]..F.R..P.D..Q[STAH].A...I |
| 16 | 2.15E+07 | L-(1,3,4)C..[FYW]A..[STAH]R..P..F.E.K.I.F.M |
| 17 | 1.40E+07 | F-(1)I.Q...[STAH][STAH]-(4)L[STAH]....[FYW]..F.R..P.D..Q..A...I |
| 18 | 1.37E+07 | L-(2,4)L...[STAH].[STAH].[STAH]-(3)LS....[FYW]..F.R..P.D..Q..A...I |
| 19 | 1.02E+07 | L...I-(1)Q....[STAH][STAH]....S....[FYW]..F.R..P.D..Q..A...I |
| 20 | 8.65E+06 | I-(1)Q....[STAH][STAH]....L.[DN]...[FYW]..F.R..P.D..Q..A...I |
| 21 | 8.19E+06 | S[STAH]-(1,2,3,4)LS[DN]...[FYW]..F.R..P.D..Q[STAH].A...I |
| 22 | 7.98E+06 | Q-(3)[STAH][STAH]....LS[DN]...[FYW]..F.R..P.D..Q..A...I |
| 23 | 6.82E+06 | F-(3)Q....[STAH][STAH]....L[STAH]....[FYW]..F.R..P.D..Q..A...I |
| 24 | 5.66E+06 | A[STAH][STAH]-(2,3)LS[DN]...[FYW]..F.R..P.D..Q..A...I |
| 25 | 5.57E+06 | F.I-(3)[STAH]..[STAH]....L[STAH]....[FYW]..F.R..P.D..Q..A...I |
| 26 | 5.18E+06 | L.L-(4)Q....[STAH]....L-(1)[DN]...[FYW]..F.R..P.D..Q..A...I |

TABLE 6-continued

The functionally relevant motif is shown in bold for G-protein coupled receptors family 3 (PROSITE I.D. PS00980). This run involved 25 sequences of about 25000 bases each at k = 25, D = 4, d = 8.

| Rank | z-score | Motif |
|---|---|---|
| 27 | 3.61E+06 | L.L-(2)I...[STAH]...[STAH]....[STAH]....[FYW]..F.R..P.D..Q..A...I |
| 28 | 3.48E+06 | [STAH].[STAH]-(1,2,3)LS[DN]...[FYW]..F.R..P.D..Q..A...I |
| 29 | 3.17E+06 | [STAH]...[STAH]...LS[DN]...[FYW].F.R..P.D..Q..A...I |
| 30 | 2.47E+06 | L.....Q-(4)[STAH][STAH]....S....[FYW]..F.R..P.D..Q..A...I |
| 31 | 2.43E+06 | V-(1,3)N.L.....I-(3)[STAH]...[STAH]....[STAH]....[FYW]..F....P.D..Q..A...I |
| 32 | 2.22E+06 | [STAH][STAH][STAH]-(1,2,3)LS....[FYW]..F.R..P.D..Q..A...I |
| 33 | 2.06E+06 | [STAH].[STAH][STAH]....LS....[FYW]..F.R..P.D..Q..A...I |
| 34 | 2.03E+06 | Y...L....C...A...R..P..F.E.K.I-(1,4)[FYW][STAH] |
| 35 | 1.99E+06 | I.Q...[STAH]-(1)[STAH]...L..[DN]...[FYW]..F....P.D..Q..A...I |
| 36 | 1.99E+06 | I.Q-(1)[STAH]...[STAH]...L..[DN]...[FYW]..F....P.D..Q..A...I |
| 38 | 1.97E+06 | F.I...[STAH]-(3)[STAH]...L..[DN]...[FYW]..F....P.D..Q..A...I |
| 40 | 1.97E+06 | F.I-(3)[STAH]..[STAH]....L..[DN]...[FYW]..F....P.D..Q..A...I |
| 41 | 1.91E+06 | [STAH]..[STAH].K-(1,4)P..FNE[STAH]K.I.F[STAH]M |
| 42 | 1.72E+06 | CC[FYW].C..C....[FYW]-(2,4)[DN]..[STAH]C..C |
| 43 | 1.57E+06 | [STAH]-(1,3,4)[FYW]A..[STAH]R..P..F.E.K.I.F.M |
| 44 | 1.49E+06 | A-(1,3)[STAH]...L[STAH][DN]...[FYW]..F.R..P.D..Q..A...I |
| 45 | 1.36E+06 | Q...[STAH].[STAH]-(3)L[STAH]....[FYW]..F.R..P.D..Q..A...I |
| 46 | 1.32E+06 | I-(3)[STAH]..[STAH][STAH].....S....[FYW]..F.R..P.D..Q..A...I |
| 47 | 1.31E+06 | [STAH][STAH]-(1,2,3,4)L.[DN]...[FYW]..F.R..P.D..Q..A...I |
| 48 | 1.24E+06 | [STAH]..[STAH][STAH]-(1,3)LS....[FYW]..F.R..P.D..Q..A...I |
| 49 | 1.19E+06 | [FYW]-(1,3,4)[STAH]...P..FNE[STAH]K.I.F[STAH]M |
| 50 | 1.12E+06 | I...[STAH]-(3)[STAH]...L[STAH]....[FYW]..F.R..P.D..Q..A...I |

TABLE 7

The functionally relevant motif is shown in bold for Chitin recognition (PROSITE I.D. PS00026). Here 53 sequences of about 13823 bases were analyzed at k = 53, D = 5, d = 10.

| Rank | z-score | Motif |
|---|---|---|
| 1 | 5.42E+06 | C-(4,5)CCS..G[FYW]CG....[FYW]C |
| 2 | 1.73E+06 | C-(4,5)CCS..G[FYW]CG.....C |
| 3 | 1.70E+06 | C-(4,5)CCS..G.CG....[FYW]C |
| 4 | 1.56E+06 | CCS..G[FYW]CG....[FYW]C |
| 5 | 544162 | C-(4,5)CCS..G.CG.....C |
| 6 | 4.95E+05 | CCS..G[FYW]CG.....C |
| 7 | 488261 | CCS..G.CG....[FYW]C |
| 8 | 155706 | CCS..G.CG.....C |
| 9 | 104666 | C-(4,5)C.S..[GASL][FYW]CG.....C |
| 10 | 84133.4 | C.....C-(3,4)[GASL][FYW]CG....[FYW]C |
| 11 | 56078 | C.....C-(3,4)G.CG....[FYW]C |

TABLE 8

The functionally relevant motif is shown in bold for Coagulation factors 5/8 type C domain (PROSITE I.D. PS01286). Here 40 sequences of about 80290 bases were analyzed. Notice that in this case, the motifs have a fairly large gap size of 10 bases at k = 40, D = 10, d = 10.

| Rank | z-score | Motif |
|---|---|---|
| 1 | 969.563 | P-(4,5,8,9,10)[LM]R.[GE][LIVP].GC |
| 2 | 694.1 | P-(4,5,8,9,10)[LM]R.[GE][LIVP].[GE]C |
| 3 | 370.594 | [LIVP]-(1,3,4,5,6,7,8,9,10)[LM]R.[GE]..[GE]C |
| 4 | 361.052 | P-(4,5,8,9,10)[LM]R.[GE]..[GE]C |
| 5 | 261.519 | [LIVP]-(1,3,4,5,6,7,8,9,10)[LM]R.[GE][LIVP]..C |
| 6 | 261.519 | [LIVP]-(1,3,4,5,6,7,8,9,10)[LM]R..[LIVP].[GE]C |
| 7 | 254.971 | P-(4,5,8,9,10)[LM]R.[GE][LIVP]..C |
| 8 | 254.971 | P-(4,5,8,9,10)[LM]R..[LIVP].[GE]C |
| 9 | 249.763 | [LIVP].......[LIVP]-(1,2,4,5,6,7,8,9,10)R.[GE]..GC |

The extensibility of a motif not only leads to a succinct description but also helps capture function and/or structure in a single pattern, which would be not possible through a rigid description. At the same time, with extensible motifs the number of candidates to be considered increases dramatically.

An exemplary embodiment of the present invention characterizes a pattern rigidly, and conjugates structure and set of occurrences. This results in a definition of motif that lends itself to a natural notion of maximality, thereby embodying statistics and structure in one measure of surprise. This is unlike all previous approaches that consider structure and statistics as separate features of a pattern.

An exemplary embodiment of the present invention provides a powerful syntactic mechanism for eliminating unimportant motifs before their score is computed. As explained above, for the class of over-represented motifs, the non-maximal motifs are not more surprising than the maximal motifs.

While the invention has been described in terms of several exemplary embodiments, those skilled in the art will recognize that the invention can be practiced with modification.

Further, it is noted that, Applicant's intent is to encompass equivalents of all claim elements, even if amended later during prosecution.

What is claimed is:

1. A method of extracting an extensible motif from a sequence, said method comprising:
   on a processing unit of a computer, assigning a significance, comprising an extensible z-score, to an extensible motif within said sequence based upon a syntactic and statistical analysis; and
   identifying an extensible motif having a significance that exceeds a predetermined threshold,
   wherein said assigning said significance comprises restricting a computation of the extensible z-score for each of said motifs to classes of maximal motifs.

2. The method of claim 1, wherein said restricting said computation of the extensible z-score comprises:
   pairwise iterating combinations of segments within said sequence to identify a maximal extensible motif; and
   pruning a maximal extensible motif which is not viable.

3. The method of claim 1, wherein said assigning said significance comprises:
   scanning the sequence to identify patterns that have two solid characters;
   storing start and end positions of the identified patterns; and combining all cells with a dot character and the same start and end solid characters to construct extensible cells.

4. The method of claim 1, wherein said assigning said significance comprises pruning by occurrences.

5. The method of claim 1, wherein said assigning said significance comprises pruning by composition.

6. A system for extracting an extensible motif from a sequence, said system comprising:
   means for assigning a significance, comprising an extensible z-score, to an extensible motif within said sequence based upon a syntactic and statistical analysis; and
   means for identifying an extensible motif having a significance that exceeds a predetermined threshold,
   wherein said means for assigning said significance comprises means for restricting a computation of the extensible z-score for each of said motifs to classes of maximal motifs.

7. The system of claim 6, wherein said means for restricting said computation of the extensible z-score comprises:
   means for pairwise iterating combinations of segments within said sequence to identify a maximal extensible motif; and
   means for pruning a maximal extensible motif which is not viable.

8. The system of claim 6, wherein said means for assigning said significance comprises:
   means for scanning the sequence to identify patterns that have two solid characters;
   means for storing start and end positions of the identified patterns; and
   means for combining all cells with a dot character and a same start and end solid characters to construct extensible cells.

9. The system of claim 6, wherein said means for assigning said significance comprises pruning by occurrences.

10. The system of claim 6, wherein said means for assigning said significance comprises pruning by composition.

11. The method of claim 1, wherein said extensible motif comprises at least one annotated dot character.

12. The method of claim 1, further comprising displaying a list of identified extensible motifs.

13. The method of claim 12, further comprising displaying statistical information for each of said displayed extensible motifs.

14. The method of claim 1, further comprising iterating said assigning said significance and said identifying said extensible motif.

* * * * *